| (12) | United States Patent | (10) Patent No.: | US 7,090,841 B1 |
| --- | --- | --- | --- |
| | O'Brien et al. | (45) Date of Patent: | Aug. 15, 2006 |

(54) USE OF CD63 INHIBITORS

(75) Inventors: William A. O'Brien, Galveston, TX (US); Kathie Grovit-Ferbas, Los Angeles, CA (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 09/846,506

(22) Filed: May 1, 2001

Related U.S. Application Data

(60) Provisional application No. 60/201,254, filed on May 1, 2000.

(51) Int. Cl.
*A61K 39/395* (2006.01)

(52) U.S. Cl. .............................. 424/130.1; 424/135.1; 424/139.1; 424/141.1; 424/142.1; 424/143.1; 424/144.1; 424/154.1

(58) Field of Classification Search ................. 514/44; 435/2, 6, 325, 375
See application file for complete search history.

(56) References Cited

OTHER PUBLICATIONS

Agrawal, S. Trends Biotechnol. Oct. 1996;14(10):376-87.*
Braasch, D. A. Biochemistry. Apr. 2002; 41(14): 4503-4510.*
Branch, A. D., (1998). Trends Biochem Sci. Feb. 1998;23(2):45-50.*
Gewirtz et al., Proc. Natl. Acad. Sci. v 93, pp. 3161-3163.*
Tamm, I. et al. The Lancet. Aug. 2001 358: 489-497.*
McCune, SL et al., (Sep. 12, 2001) JAMA 286(10) 1149-1152.*
Smith et al. Mol. Immunol. 1995. vol. 32, No. 17/18, pp. 1339-1344.*
Audran at L., Immun. Meth. 1995, 188:147-154.*

* cited by examiner

*Primary Examiner*—James Schultz
(74) *Attorney, Agent, or Firm*—Rogalskyj & Weyand, LLP

(57) ABSTRACT

The invention provides a method of decreasing human immunodeficiency virus entry into cells, the method comprising decreasing levels of functional CD63 present with the human immunodeficiency virus and the cells. The invention further provides a method of treating or preventing human immunodeficiency virus infection in a subject, the method comprising administering to the subject an amount of a compound effective to decrease levels of functional CD63 in the cells of the subject.

1 Claim, No Drawings

USE OF CD63 INHIBITORS

This application claims priority of U.S. Provisional Patent Application No. 60/201,254, filed May 1, 2000.

This invention was made with support from the United States Government under Grant No. RO1NS35705. The U.S. Government may have certain rights in this invention.

FIELD OF THE INVENTION

The subject invention is directed generally to a method for treating or preventing human immunodeficiency virus (HIV) infection, by decreasing HIV entry into cells, and more particularly to decreasing levels of functional CD63 present within the HIV and the cells in order to decrease HIV entry into cells.

BACKGROUND OF THE INVENTION

Throughout this application various publications are referenced. The disclosures of each of these publications in their entireties are hereby incorporated by reference in this application.

Macrophages (MØ) are crucial for human immunodeficiency virus type 1 (HIV) pathogenesis. In addition to their antigen presenting function, these cells appear to be important targets for HIV infection in extravascular tissues. Nearly all primary HIV strains are capable of replication in MØ, and the overwhelming predominance of macrophage (M)-tropic virus strains early in disease suggest that these cells may be involved in virus transmission, particularly for sexually acquired infection.

Substantial work has been accomplished over the last decade to define molecular determinants of M-tropism; identification of particularly the β chemokine receptor CCR5 as an HIV co-receptor required for efficient entry of M-tropic HIV strains into MØ, as well as CD4+ T cells. Specific mechanisms of entry into primary MØ remain poorly defined, however. Although CD4 and CXCR4 are expressed on MØ and can be utilized for entry, viruses that use CD4 and CCR5 (R5 strains) infect MØ more efficiently than those using CD4 and CXCR4 (X4 strains). T-tropic HIV strains that use CD4 and CCR5 that do enter MØ, however, may fail to replicate in an Env-dependent manner. Efficiency of HIV infection may therefore involve cellular factors in addition to CD4 and chemokine receptors.

Treatment of HIV infection dramatically improved in 1996 with the approval of protease inhibitors, and the routine use of combinations of three or four antiretroviral drugs simultaneously. Despite initial success resulting in suppression of virus replication below limits of quantification in the majority of patients (Gulick 1998; Staszewski 1999), limitations of this approach are becoming increasingly apparent. Only about half of patients initiating combination antiretroviral therapy will have a durable virologic response. Response to subsequent regimens is complicated by cross resistance within the available classes of drugs, limited exclusively to protease inhibitors and reverse transcriptase inhibitors. Prototype small molecule inhibitors of chemokine receptor interactions, and of gp41-mediated fusion are directed to envelope-specific events in the HIV life cycle, opening the era of development of a new class of antiretroviral drugs, inhibitors of HIV entry.

Identification of novel cellular factors involved in HIV entry could provide important new therapeutic targets, and expand the arsenal of drugs that can be used in combination to block HIV entry. This class of antiretroviral drugs would still be active in patients who have developed resistance to protease inhibitors and reverse transcriptase inhibitors.

SUMMARY OF THE INVENTION

To this end, the subject invention provides a method of decreasing human immunodeficiency virus (HIV) entry into cells, the method comprising decreasing levels of functional CD63 present within the HIV and the cells. The invention further provides a method of treating or preventing human immunodeficiency virus infection in a subject, the method comprising administering to the subject an amount of a compound effective to decrease levels of functional CD63 in cells of the subject.

DETAILED DESCRIPTION OF THE INVENTION

The subject invention is based on the discovery that CD63 is a cofactor for HIV entry into macrophages. As such, decreasing levels of functional CD63 present with HIV and the cells (the macrophages, for example)(such as by decreasing CD63 gene expression or by decreasing activity of CD63) can decrease human immunodeficiency virus entry into the cells.

Decreasing "levels" of functional CD63 refers to decreasing expression of the CD63 gene, or decreasing activity of the CD63 protein.

The invention thus provides a method of decreasing human immunodeficiency virus entry into cells, the method comprising decreasing levels of CD63 present with the HIV and the cells. The invention further provides a method of treating or preventing HIV infection in a subject, the method comprising administering to the subject an amount of a compound effective to decrease levels of functional CD63 in cells of the subject.

Levels of CD63 can be decreased by various methods, at the gene and protein levels. In one embodiment, the levels are decreased by decreasing CD63 gene expression of the CD63 protein in cells. This can be accomplished by exposing the cells to a compound which decreases CD63 gene expression of the CD63 protein. The compound could be, for example, an antisense oligonucleotide targeted to the CD63 gene.

In a similar embodiment, the compound which decreases CD63 gene expression of the CD63 protein could be a ribozyme, which is a special category of antisense RNA molecule having a recognition sequence complementary to the mRNA encoding the CD63. A ribozyme not only complexes with a target sequence via complementary antisense sequences, but also catalyzes the hydrolysis, or cleavage, of the template mRNA molecule. The expression of the CD63 protein is therefore prevented.

Other methods for decreasing CD63 gene expression could also involve site-directed mutagenesis of the CD63 gene to prevent expression of the CD63, or various gene therapy techniques. It may be desirable to alter the expression of the CD63 gene in such a way that expression of the CD63 is inducible, allowing the controlled increase or decrease in expression of CD63.

Levels, in particular activity, of CD63 can also be decreased by exposing the CD63 to an inhibitor of the CD63. Such inhibitors could be antibodies directed to CD63, or chemical inhibitors of CD63 activity. Other inhibitors of CD63 could also readily be identified by various screening methods used in the art (see more detailed discussion below). In addition to chemical inhibitors, peptide inhibitors could also be identified with currently known screening methods (for example, using phage display libraries and other peptide screening methods).

Since the method of the subject invention is a method of decreasing human immunodeficiency virus entry into cells (and therefore also a method of treating or preventing HIV infection in a subject), the cells of interest are primarily human cells. However, cells of animal origin may also be of interest for primarily research purposes. The method is useful in vitro or in vivo, for research and development and for therapeutic purposes.

In one embodiment, the invention employs oligonucleotides targeted to nucleic acids encoding functional CD63. The relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. In the subject invention, this may be, for example, the cellular gene (or mRNA made from the gene) for CD63; i.e., the target is a nucleic acid encoding CD63, the CD63 gene, or mRNA expressed from the CD63 gene. The targeting process also includes determination of a site or sites within the nucleic acid sequence for the oligonucleotide interaction to occur such that the desired effect, modulation of gene expression, will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of CD63 gene expression is presently the preferred form of modulation. This modulation can be measured in ways which are routine in the art, for example by Northern blot assay of mRNA expression or Western blot assay of protein expression. Effects on HIV entry can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In various embodiments of this invention, oligonucleotides are provided which are targeted to mRNA encoding CD63. In accordance with this invention, persons of ordinary skill in the art will understand that mRNA includes not only the coding region which carries the information to encode a gene product using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. The functions of mRNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with CD63 gene expression.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The compounds and/or inhibitors used in the methods of the subject invention encompass any pharmaceutically acceptable salts, esters, or salts of such esters, or any other compound/inhibitor which, upon administration to an animal including a human, is capable of providing (directly or indirectly) the biologically active metabolite or residue thereof. Accordingly, for example, the disclosure is also drawn to prodrugs and pharmaceutically acceptable salts of the compounds and/or inhibitors used in the subject invention, pharmaceutically acceptable salts of such prodrugs, and other bioequivalents.

In regard to prodrugs, the compounds and/or inhibitors for use in the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions.

In regard to pharmaceutically acceptable salts, the term pharmaceutically acceptable salts refers to physiologically and pharmaceutically acceptable salts of the compounds and/or inhibitors used in the subject invention: i.e., salts that retain the desired biological activity of the parent compound and do not impart undesired toxicological effects thereto.

The oligonucleotides used in the method of the subject invention preferably are from about 8 to about 50 nucleotides in length. In the context of this invention it is understood that this encompasses non-naturally occurring oligomers, preferably having 8 to 50 monomers.

The oligonucleotides used in accordance with this invention may be conveniently and routinely made through the well-known technique of solid phase synthesis.

Equipment for such synthesis is sold by several vendors including Applied Biosystems. Any other means for such synthesis may also be employed; the actual synthesis of the oligonucleotides is well within the skill of the art. It is also well known to use similar techniques to prepare other oligonucleotides such as the phosphorothioates and alkylated derivatives. It is also well known to use similar techniques and commercially available modified amidites and controlled-pore glass (CD63G) products such as biotin, fluorescein, acridine or psoralen-modified amidites and/or CD63G (available from Glen Research, Sterling Va.) to synthesize fluorescently labeled, biotinylated or other modified oligonucleotides such as cholesterol-modified oligonucleotides.

In the context of this invention, to "expose" cells (including the cells of tissues) to a compound and/or inhibitor means to add the compound and/or inhibitor, usually in a liquid carrier, to a cell suspension or tissue sample, either in vitro or ex vivo, or to administer the compounds and/or inhibitor to cells or tissues within an animal (including a human) subject.

For therapeutics, methods of decreasing human immunodeficiency virus entry into cells and methods of preventing and treating human immunodeficiency virus infection are provided. The formulation of therapeutic compositions and their subsequent administration is believed to be within the skill in the art. In general, for therapeutics, a patient suspected of needing such therapy is given a compound and/or inhibitor in accordance with the invention, commonly in a pharmaceutically acceptable carrier, in amounts and for periods which will vary depending upon the nature of the particular disease, its severity and the patient's overall condition. The pharmaceutical compositions may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is LIPOFECTIN™ (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual compounds and/or inhibitors, and can generally be calculated based on $IC_{50}$'s or $EC_{50}$'s or viral infectivity levels in in vitro and in vivo animal studies. For example, given the molecular weight of a compound (derived from oligonucleotide sequence and/or chemical structure) and an effective dose such as an $IC_{50}$, for example (derived experimentally), a dose in mg/kg is routinely calculated.

The nucleic acid and amino acid sequence of CD63 genes are known and readily available from GenBank and described in the literature. See, for example, GenBank Accession Nos. NM 001780 and NP 001771 (human CD63) and Nos. NMNM 007653 and $NPO_{31679}$ (house mouse Cd63); Hotta et al., Biochem Biophys Res Commun 185(1): 436–442 (1992)(human CD63); Miyamoto et al., Biochim Biophys Acta 1217(3):312–316 (1994)(mouse Cd63).

Given these sequences, one can design appropriate antisense molecules for use in the subject invention. Furthermore, by expressing the functional CD63 in a host cell, one can screen for suitable compounds and/or inhibitors for use in the subject invention. The function of the encoded CD63 can be assayed according to methods known in the art. As used herein, "functional" expression refers to the synthesis and any necessary post-translational processing of a CD63 molecule in a cell so that the CD63 is active.

More particularly, having known nucleic acid molecules encoding the CD63, a method for screening a chemical agent (compound or inhibitor) for the ability of the chemical agent to modify CD63 function begins by introducing the nucleic acid molecule encoding the CD63 into a host cell, and expressing the CD63 encoded by the molecule in the host cell. The expression results in the functional expression of a CD63 in the host cell. The cell is then exposed to a chemical agent and evaluated to determine if the chemical agent modifies the function of the CD63. From this evaluation, chemical agents effective in altering the function of the CD63 can be found and utilized in the methods of the subject invention.

Drugs, such as peptide drugs, which inhibit the CD63 can be made using various methods known in the art. Initially, a monoclonal antibody can be prepared which specifically hybridizes to the CD63, thereby interfering with activity.

The monoclonal antibodies can be produced by hybridomas. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell, A. M., "Monoclonal Antibody Technology: Laboratory Techniques in Biochemistry and Molecular Biology", Elsevier Science Publishers, Amsterdam, The Netherlands (1984); St. Groth, et al., J Immunol Methods 35:1–21 (1980)). Any animal (mouse, rabbit, etc.) which is known to produce antibodies can be immunized with the CD63 (or an antigenic fragment thereof). Methods for immunization are well known in the art. Such methods include subcutaneous or intraperitoneal injection of the CD63. One skilled in the art will recognize that the amount of the CD63 used for immunization will vary based on the animal which is immunized, the antigenicity of the CD63, and the site of injection.

The CD63 which is used as an immunogen may be modified or administered in an adjuvant in order to increase the CD63's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz, et al., Exp Cell Res 175:109–124 (1988)).

Hybridomas secreting the desired antibodies are cloned and the class and subclass are determined using procedures known in the art (Campbell, A. M., "Monoclonal Antibody Technology: Laboratory Techniques in Biochemistry and Molecular Biology", Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

Once a monoclonal antibody which specifically hybridizes to the CD63 is identified, the monoclonal (which is itself a compound or inhibitor which can be used in the subject invention) can be used to identify peptides capable of mimicking the inhibitory activity of the monoclonal antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., Gene 73:305–318 (1988)). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley, S. F. & Smith, G. P., Gene 73:305–318 (1988); Cwirla, S. E., et al., Proc Natl Acad Sci USA 87:6378–6382 (1990); Scott, J. K. & Smith, G. P., Science 249:386–390 (1990); Christian, R. B., et al., J Mol Biol 227:711–718 (1992); Smith, G. P. & Scott, J. K., Methods in Enzymology 217:228–257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., Gene 73:305–318 (1988); Scott, J. K., Trends in Biochem Sci 17:241–245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally-occurring molecule, i.e. a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes CD63 can be identified. The sequences of these mimotopes represent short peptides which can then be used in various ways, for example as peptide drugs that bind to CD63 and decrease the activity of CD63. Once the sequence of the mimotope is determined, the peptide drugs can be chemically synthesized.

The peptides for use in the subject invention can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptide depends, in part, on the desired characteristics of the peptide. For example, the incorporation of one or more (D)-amino acids can confer increased stability on a peptide and can allow a peptide to remain active in the body for an extended period of time. The incorporation of one or more (D)-amino acids can also increase or decrease the pharmacological activity of a peptide.

The peptide may also be cyclized, since cyclization may provide the peptide with superior properties over their linear counterparts.

Modifications to the peptide backbone and peptide bonds thereof are encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC 46:257 (1981) and Raucher et al., Tetrahedron Lett 21:14061 (1980). An amino acid mimic is, therefore, an organic molecule that retains the similar amino acid pharmacophore groups as are present in the corresponding amino acid and which exhibits substantially the same spatial arrangement between functional groups.

The substitution of amino acids by non-naturally occurring amino acids and amino acid mimics as described above can enhance the overall activity or properties of an individual peptide thereof based on the modifications to the backbone or side chain functionalities. For example, these types of alterations can enhance the peptide's stability to enzymatic breakdown and increase biological activity. Modifications to the peptide backbone similarly can add stability and enhance activity.

One skilled in the art, using the identified sequences can easily synthesize the peptides for use in the invention. Standard procedures for preparing synthetic peptides are well known in the art. The novel peptides can be synthesized using: the solid phase peptide synthesis (SPPS) method of Merrifield, J Am Chem Soc 85:2149 (1964) or modifications of SPPS; or, the peptides can be synthesized using standard solution methods well known in the art (see, for example, Bodanzsky, "Principles of Peptide Synthesis", 2d Ed., Springer-Verlag (1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc Natl Acad Sci USA 82:5131 (1985).

EXAMPLE I

CD63, a member of the tetraspan transmembrane protein family, which includes CD9, CD81 and CD82, is involved in HIV entry into MØ. To identify cell-associated molecules that are important for MØ tropism, a monoclonal antibody (mAb) library was screened to determine whether antibodies to characterized MØ-specific antigens can block HIV entry. It is noteworthy that four independently derived mAb specific for CD63 all blocked HIV entry into MØ. CD63 has been characterized as an activation/differentiation marker on a wide variety of cells, particularly platelets, and also is a melanoma-associated antigen (Hotta 1998; Metzelaar 1991). CD63 antigen is associated with beta-1 integrins, MHC antigens and with other tetraspan integral membrane proteins (Hammond 1998; Mannion 1996; Rubinstein 1996), but no biological function of the CD63 antigen is known at present. In neutrophils, CD63 is an activation antigen in that its surface expression is upregulated from intracellular stores by cytokine stimulation. Binding by one CD63 mAb has been reported to increase neutrophil adhesion to LPS-stimulated endothelial cells mediated by CD11/CD18 (Skubitz 1996). CD63 mAb binding appears to trigger a transient activation signal that requires extracellular calcium, regulates the adhesive activity, increases surface expression of CD11/CD18 and down-regulates expression of CD62L. The associated tyrosine protein kinase activity may play a role in signal transduction by CD63 to regulate other cell functions (Skubitz 1996). Another tetraspan membrane protein, CD81, has been proposed as a receptor for HCV (Pileri 1998), and anti-CD82 can stimulate IL-2 production through costimulation with anti-CD3 (Lebel-Binay 1995). Anti-CD82 appears to also inhibit syncytium formation induced by human T cell leukemia virus type I (HTLV-1), without affecting virus binding (Imai 1992). HTLV-1 is another human retrovirus that also infects CD4+ T cells, inducing leukemia rather than immunodeficiency. Antibody did not block binding of virions, suggesting involvement of CD82 antigen in post-binding fusion processes.

EXAMPLE II

Inhibitors of CXCR4 can be used to block HIV entry. Inhibition of chemokine receptor interactions is an exciting mode of antiretroviral therapy. HIV entry in cultured CD4+ cells was inhibited by use of a small peptide inhibitor of CXCR4 interactions, ALX40–4C (ALX)(Doranz 1997). M-tropic R5 strains are resistant to this inhibitor. Studies prior to identification of chemokine receptors as HIV coreceptors demonstrated that ALX-mediated blockade of infection with T cell line-adapted HIV strains involves the V3 loop (OBrien 1996).

To further define the effects of ALX, luciferase reporter viruses (Connor 1995) based on a common NL4-3 HIV core with the 2.0 kb luciferase gene substituted in place of nef were used. This was pseudotyped with different Env proteins, with virus entry indicated by relative light units (RLU). Reporter viruses, pseudotyped with the T-tropic Envs NL4-3 and HXB2 (X4), the M-tropic Env ADA (R5, uses CCR5), or the amphotropic murine leukemia virus (MLV) Env that enters cells independently of CD4 or chemokine receptor, were used to infect PM1 cells, a T-cell line that expresses CD4, CXCR4 and CCR5 (Deng 1996). Anti-CD4 (Leu3a) inhibited all 3 HIV strains, but ALX only blocked entry of strains which use CXCR4.

EXAMPLE III

Screen for novel cellular factors involved in HIV entry in MØ by mAb identified CD63. Adherence of blood monocytes to plastic activates and causes differentiation of MØ, associated with a variety of cellular changes that lead to increased HIV replication. Over the first 7 days of adherence, cell surface expression of CCR5 gradually increases, but CD4 and CXCR4 expression levels remain fairly constant (Chen 1996; Dimarzio 1998; Jabbar 1990; Lee 1999). Although changes in CCR5 expression are consistent with observed increases in susceptibility to HIV infection (Day 6 or 7) other cellular factors whose expression is increased with adherence may also be involved in determining HIV susceptibility.

In preliminary studies initiated prior to identification of these coreceptors, the myeloid monoclonal antibody (mAb) library (N=120) of the 5th International Workshop on Human Leukocyte Differentiation Antigens was screened. Since MØ show increased permissiveness to HIV infection after 6 days of adherence to plastic (Rich 1992), this library was screened to identify antibodies that bound better to MØ cultured 6 days, compared with those cultured 3 days. Of those mAb found to bind MØ(N=56), there were 15 mAb that exhibited >30% increases in mean channel fluorescence at day 6 compared with day 3.

These 15 mAbs were used in infectivity assays to determine whether they were capable of blocking entry of HIV-SX, an NL4-3-based chimeric clone expressing JR-FL envelope (Obrien 1990), into 7 day-adherent MØ, as measured by quantitative HIV DNA PCR assay. There were 6 mAb that reduced virus entry, but antigen targets for two of these mAb (M8 and MC7) have not been identifed. Surprisingly, the other four mAbs were all directed toward one molecule. CD63. CD63 is a tetraspan membrane glycoprotein, best known as a platelet activation marker, and as a tumor marker for malignant melanoma (Metzelaar 1991; Radford 1995). One hour pretreatment with 2 separate commercial anti-CD63 mAbs inhibited virus production as measured by extracellular p24 production in MØ for the prototypic M-tropic R5 strain HIV-SX. Pretreatment with anti-CD63 treatment also inhibited MØ entry (as measured by new HIV DNA production) and virus production of both HIV BaL and HIV-SX in a dose-dependent manner.

Studies were also initiated to examine the effects of anti-CD63 inhibition on dual tropic or R5X4 strains. The prototypic dual tropic strain 89.6 was shown to be resistant to anti-CD63 in MØ as well as to inhibition of CXCR4 interactions with AMD3100. If these inhibitors are used together, however, good inhibition is obtained, further supporting the CCR5-dependance of anti-CD63 inhibition. In infection using a different R5X4 HIV strain, 96USNG31, HIV inhibition was seen following treatment with either AMD3100 or anti-CD63 alone, but in repeat experiments, combination treatment with anti-CD63 and AMD3100 together is necessary for consistent inhibition of HIV entry. This suggests that there may be differences in CXCR4 and CCR5-dependent pathways for HIV entry in macrophages from different individuals. In another inhibition experiment done simultaneously in cells from two donors using the R5 strain HIV-SX, anti-CD63 inhibited HIV infection, but CD82 blocked HIV-SX in one donor, but not the other.

EXAMPLE IV

Cell specificity of anti-CD63 inhibition of HIV infection. Preliminary studies suggest that anti-CD63 inhibition is restricted to CCR5-mediated entry pathways, both for R5 and for R5X4 isolates. It is relevant to also test cell dependence of anti-CD63 inhibition in anticipation of use of CD63 inhibition as a treatment modality. R5 strains are the most prevalent of primary HIV isolates, and readily infect both MØ and CD4+ lymphocytes. The ability of anti-CD63 to inhibit HIV replication in MØ and PBL derived from the same donor was therefore assessed. Although anti-CD63 consistently inhibited HIV entry of the M-tropic SX strain in MØ, PBL are resistant to this inhibition, even when using large amounts of anti-CD63 (25 µg/ml). Anti-CD4 inhibits infection of both cell types (used as a positive control), and although there is some reduction in infectivity with the isotype control antibody, this is a relatively minor effect. There are several important differences between MØ and PBL that may explain differences in antibody inhibition. One of the most striking differences is the level of CD4 expression, with fairly low expression of CD4 in MØ (Lee 1999).

To determine whether coreceptor expression (CCR5) is acutely affected by antibody incubation, MØ were treated with anti-CD63 or an isotype control IgG antibody (which did not block HIV entry) and only small differences in CCR5 expression were found. Effects of anti-CD63 on either CCR5 or CD4 expression are unlikely given the brief duration of treatment, and because inhibition can be achieved using multiple mAb to CD63. Although virions can incorporate cellular proteins such as HLA-DR and CD63 during virus budding from cells (Arthur 1992; Orentas 1993), preincubation of virus with anti-CD63 did not inhibit HIV replication as well as preincubation of cells. The lack of sensitivity of CD4+ lymphocytes argues further against inhibition of HIV infection via viral CD63.

EXAMPLE V

HIV Env-mediated fusion in QT6 cells expressing CD4 and CCR5 is increased with co-expression of CD63. Support for a role of CD63 in HIV entry is provided by the demonstration of increased fusion or entry with introduction or overexpression of CD63. To identify cells expressing low levels of CD63, various cell lines were screened using anti-CD63 and flow cytometry. Most cells express this antigen, however, including MØ, and essentially all monocytoid or T cell lines. Previous reports suggested low CD63 expression in Raji cells (Mannion 1996), but few other cell types. The cell lines 293T, HeLaCD4, HUT78 and U937 cells all expressed high levels of CD63. Raji cells expressed low but readily detectable levels, however quail QT6 cells had very low levels of CD63 expression. These cells are very useful for fusion assays, and were used to study the role of CD63 in HIV Env-mediated fusion.

To study the effect of CD63 expression on HIV-mediated fusion in QT6 cells, a QT6 expression vector was generated. RNA was purified from stimulated PBL and cDNA for CD63 was generated by RT-PCR using primers based on the sequence in the published literature. The cDNA fragment was subcloned into a TA vector (pcDNA3.1/V5/HIS-TOPO®, Invitrogen). In this construct, CD63 is expressed as a fusion protein with a V5 tag, for use in immunoblot analysis. A similar construct was prepared without the V5 fusion protein. Following transfection of QT6 cells, CD63 expression is readily detected by flow cytometry.

QT6 cells transfected to express CD4 and T7-driven luciferase alone were unable to mediate fusion with QT6 fusion partners infected by vaccinia virus recombinants to express T7 RNA polymerase and envelopes from JR-FL (R5), HXB (X4) or 89.6 (X4R5). Transfection of CD4 and CCR5 allowed fusion of JR-FL and to a lesser extent 89.6, but not HXB. Conversely, co-expression of CD4 and CXCR4 did not induce fusion with JR-FL envelope, but did with both HXB and 89.6. Cotransfection of CD63 together with CCR5 and CD4 increased JR-FL Env-induced fusion approximately two fold, but did not affect fusion mediated by Env from 89.6 or HXB. CD63 coexpression had no effect on CXCR4-dependent cell fusion. In another fusion experiment, this time using the envelope from the R5 virus ADA, co-expression of the CD63 together with CD4 and CCR5 increased ADA Env-mediated fusion nearly four fold, but again did not effect CXCR4-dependent fusion induced by or HXB. These studies suggest that CD63 mediated fusion is linked to CCR5 and not to CXCR4, and in one experiment, enhancement of fusion mediated by Env from the dual tropic virus 89.6 was not seen.

To verify expression of HIV coreceptors and CD63 following transfection, quantitative FACS (QFACS) was used. Interestingly, CD63 expression resulted in increased CD4 expression, suggesting that CD63 may markedly stabilize CD4 on the cell surface, or be involved in CD4 turnover.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES

Arthur et al., Science 258:1935–1938 (1992).
Chen et al., J Virol 70:6044–6053 (1996).
Connor et al., Virology 206:935–944 (1995).
Deng et al., Nature 381:661–666 (1996).
DiMarzio et al., AIDS Res Hum Retroviruses 14:129–128 (1998).
Doranz et al., J Exp Med 186:1395–1400 (1997)
Gulick et al., JAMA 280:35–51 (1998).
Hammond et al., J Immunol 161:3282–3291 (1998).
Hotta et al., Cancer 48:2955 (1988).
Imai et al., J Immunol 149:2879–2886 (1992).
Jabbar et al., J Virol 64:6297–6304 (1990).
Lebel-Binay et al., J Immunol 155:101–110 (1995).
Lee et al., PNAS USA 96:5215–5220 (1999).
Mannion et al., J Immunol 157:2039–2047 (1996).
Metzelaar et al., J Biol Chem 266:3239 (1991).
O'Brien et al., Nature (London) 348:69–73 (1990).
O'Brien et al., J Virol 70:2825–2831 (1996).
Orentas et al., AIDS Res Hum Retroviruses 9:1157–1165 (1993).
Pileri et al., Science 282:938–941 (1998).
Radford et al., International Journal of Cancer 62:631–635 (1995).

Rich et al., J Clin Invest 89:176–183 (1992).
Rubinstein et al., European J Immunol 26:2657–2665 (1996).
Skubitz et al., J Immunol 157:3617–3626 (1996).
Staszewski et al., N Engl J Med 341:1865–1873 (1999).

What is claimed is:

1. A method of decreasing CD63 facilitated human immunodeficiency virus entry into macrophage cells of a subject, the method comprising identifying a subject infected with a strain of HIV and exposing the cells of the subject to an anti-CD63 antibody in an amount effective to bind the anti-CD63 antibody to CD63 present in the cells, whereby the CD63 facilitated human immunodeficiency virus entry into the cells is decreased.

* * * * *